(12) United States Patent
Morikawa et al.

(10) Patent No.: US 7,324,622 B2
(45) Date of Patent: Jan. 29, 2008

(54) RADIATION COMPUTED TOMOGRAPHY APPARATUS AND TOMOGRAPHIC IMAGE PRODUCING METHOD

(75) Inventors: Kotoko Morikawa, Tokyo (JP); Akira Hagiwara, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 176 days.

(21) Appl. No.: 10/827,932

(22) Filed: Apr. 20, 2004

(65) Prior Publication Data

US 2004/0208277 A1  Oct. 21, 2004

(30) Foreign Application Priority Data

Apr. 21, 2003 (JP) ............................. 2003-115407

(51) Int. Cl.
*G01N 23/00* (2006.01)
(52) U.S. Cl. ........................................... 378/4; 378/15
(58) Field of Classification Search .................... 378/4, 378/13–15, 901
See application file for complete search history.

(56) References Cited

U.S. PATENT DOCUMENTS

| | | | |
|---|---|---|---|
| 5,727,041 A | | 3/1998 | Hsieh |
| 5,812,628 A | | 9/1998 | Hsieh |
| 5,970,112 A | | 10/1999 | Hsieh |
| 6,061,421 A | | 5/2000 | Hagiwara |
| 6,418,184 B1 | * | 7/2002 | Wang et al. ................... 378/15 |
| 6,445,764 B2 | | 9/2002 | Gohno et al. |
| 6,539,074 B1 | * | 3/2003 | Yavuz et al. .................... 378/4 |
| 6,826,251 B1 | * | 11/2004 | Miyazaki et al. ............. 378/15 |

FOREIGN PATENT DOCUMENTS

| | | |
|---|---|---|
| EP | 0569238 A | 5/1993 |
| EP | 0569238 A1 * | 6/1993 |
| JP | 10080419 | 3/1998 |
| JP | 11239577 | 9/1999 |
| JP | 2002-336239 | 11/2002 |

OTHER PUBLICATIONS

European Search Report with Search Completed on Aug. 11, 2004, European Patent Application No. EP 04 252261, 2 pgs.

* cited by examiner

*Primary Examiner*—Hoon Song
(74) *Attorney, Agent, or Firm*—Armstrong Teasdale LLP (57) ABSTRACT

A computed tomography (CT) imaging system for improving the image quality of a tomographic image at a predefined image production position in a subject's axis direction in tomographic image reconstruction by axial scanning. The CT system includes an X-ray tube and a detector array configured to conduct a plurality of scans for detecting X-rays passing through a region to be examined around an axis AX of the region to be examined at different positions along the subject's axis Ax direction; and for each of the plurality of scans, and a reconstructing section configured to calculate and reconstruct data for tomographic images of the region to be examined at a position corresponding to a detector row in the axis direction based on detected data acquired in that scan, and combine the data for the plurality of reconstructed tomographic images to generate data for a combined tomographic image at the position corresponding to the detector row.

12 Claims, 10 Drawing Sheets

RADIATION COMPUTED TOMOGRAPHY
APPARATUS AND TOMOGRAPHIC IMAGE
PRODUCING METHOD

CROSS REFERENCE TO RELATED
APPLICATIONS

This application claims the benefit of Japanese Application No. 2003-115407 filed Apr. 21, 2003.

BACKGROUND OF THE INVENTION

The present invention relates to a radiation computed tomography apparatus (referred to as a radiation CT apparatus hereinbelow) and a tomographic image producing method for calculating a tomographic image of a subject from radiation projection data on the subject.

Known radiation CT apparatuses include an X-ray CT apparatus employing X-rays as radiation, for example. Known X-ray CT apparatuses include an apparatus comprising a plurality of X-ray detectors arranged in a two-dimensional manner. The plurality of X-ray detectors are disposed to have a width in a direction along a predefined axis with respect to a subject. Since rows of X-ray detectors are formed in the axis direction in the predefined width, the X-ray detectors arranged in a two-dimensional manner are generally referred to as a multi-row detector.

One known technique for reconstructing a tomographic image employing the multi-row detector is a cone BP (backprojection) process (see Patent Document 1, for example).

When using the cone BP process in the X-ray CT apparatus having the multi-row detector, the multi-row detector is rotated once around an axis as cone-shaped X-rays having a fan-shaped cross section orthogonal to the axis are emitted, for example. X-rays passing through the subject are then detected by the multi-row detector to thereby scan a region to be examined in the subject. After one scan has been completed, the multi-row detector is shifted in the axis direction at a predefined pitch, and a next scan is conducted. Such a scan technique is generally referred to as axial scanning. Since the plurality of rows of X-ray detectors lie in the axis direction, a number, corresponding to the number of rows of X-ray detectors, of tomographic images of the subject can be obtained in one scan.

Production of a tomographic image corresponding to a row of the X-ray detectors by the cone BP process uses not only detected data obtained by that row of X-ray detectors but those from X-rays passing through the region to be examined corresponding to the tomographic image and detected by the other rows of X-ray detectors. By thus increasing the amount of data for image production, the image quality of the tomographic image can be improved to some degree.

[Patent Document 1]

Japanese Patent Application Laid Open No. 2002-336239.

In the conventional cone BP process, however, the amount of detected data usable for image production is reduced in producing tomographic images corresponding to the detector rows lying at the ends in the axis direction. Thus, a need to further improve image quality exists especially for tomographic images corresponding to the detector rows at the ends.

Moreover, a tomographic image is produced using only detected data acquired in one scan around the subject's axis in the conventional cone BP process. Therefore, in an axial scan, data continuity is poor between a tomographic image acquired in a scan at one position in the axis direction and that acquired in another scan at another position. Such poor data continuity results in disadvantages such as that there is an adverse effect on the image quality of a tomographic image obtained by multiplanar reformation (MPR) using a plurality of other tomographic images orthogonal to the axis direction obtained by the cone BP process. An example of the disadvantages is insufficient smoothness in the MPR image obtained by the multiplanar reformation, in which banding artifacts occur in a portion corresponding to the border between the scans.

SUMMARY OF THE INVENTION

It is an object of the present invention to provide a radiation computed tomography apparatus (radiation CT apparatus) that can improve the image quality of a tomographic image at a predefined image production position in a subject's axis direction in tomographic image reconstruction by axial scanning. It is also an object of the present invention to provide a tomographic image producing method for use in the radiation CT apparatus, which method can improve the image quality of a tomographic image at an image production position.

A radiation computed tomography apparatus in accordance with the present invention comprises: a radiation detecting apparatus for conducting a plurality of scans for detecting radiation passing through a region to be examined around a predefined axis of said region to be examined at different positions along said predefined axis direction; and image reconstructing means for obtaining a plurality of sets of data for the same position in said region to be examined based on detected data acquired in said plurality of scans, and reconstructing data for one tomographic image of the region to be examined at an image production position in said predefined axis direction based on said plurality of sets of data.

The radiation computed tomography apparatus in accordance with the present invention may have a configuration comprising: a radiation detecting apparatus for conducting a plurality of scans for detecting radiation passing through a region to be examined around a predefined axis of said region to be examined at different positions along said predefined axis direction; and image reconstructing means for, for each of said plurality of scans, reconstructing data for a tomographic image of the region to be examined at an image production position in said predefined axis direction by a calculation based on detected data acquired in said scan, combining said reconstructed data for a plurality of tomographic images to generate data for a combined tomographic image at said image production position.

A tomographic image producing method in accordance with the present invention comprises the steps of: conducting a plurality of scans for detecting radiation passing through a region to be examined around a predefined axis of said region to be examined at different positions along said predefined axis direction; and obtaining a plurality of sets of data for the same position in said region to be examined based on detected data acquired in said plurality of scans, and calculating and reconstructing data for one tomographic image of the region to be examined at an image production position in said predefined axis direction based on said plurality of sets of data.

The tomographic image producing method in accordance with the invention may have a configuration comprising the steps of: conducting a plurality of scans for detecting radiation passing through a region to be examined around a predefined axis of said region to be examined at different positions along said predefined axis direction; for each of said plurality of scans, calculating and reconstructing data for a tomographic image of the region to be examined at an image production position in said predefined axis direction based on detected data acquired in said scan; and combining said reconstructed data for a plurality of tomographic images to generate data for a combined tomographic image at said image production position.

According to the present invention, a radiation detecting apparatus detects radiation passing through a region to be examined around a predefined axis of the region to be examined to thereby scan the region to be examined. The radiation detecting apparatus conducts a plurality of scans on the region to be examined at different positions along the axis direction. Detected data of the radiation passing through the region to be examined is acquired in each of the plurality of scans. Image reconstructing means obtains a plurality of sets of data at the same position in the region to be examined based on the detected data acquired in the plurality of scans. The image reconstructing means calculates and reconstructs data for a tomographic image of the region to be examined at a predefined image production position in the axis direction based on the plurality of sets of data.

At that time, the image reconstructing means reconstructs data for a tomographic image of the region to be examined at the image production position from the detected data acquired in the plurality of scans. The image reconstructing means combines data for the plurality of tomographic images acquired corresponding to the number of scans at the image production position to generate data for a combined tomographic image. The data for the combined tomographic image is final tomographic image data of the region to be examined at the image production position.

Therefore, the present invention provides a radiation computed tomography apparatus that can improve the image quality of a tomographic image at a predefined image production position in a subject's axis direction in tomographic image reconstruction by axial scanning. The present invention also provides a tomographic image producing method for use in the radiation CT apparatus, which method can improve the image quality of a tomographic image at an image production position.

Further objects and advantages of the present invention will be apparent from the following description of the preferred embodiments of the invention as illustrated in the accompanying drawings.

BRIEF DESCRIPTION OF THE DRAWINGS

FIG. 8(*a*) shows in the yz-plane a plurality of combined tomographic images produced in the z-direction, and FIG. 8(*b*) shows an exemplary MPR image in the yz-plane produced using the plurality of combined tomographic images.

DETAILED DESCRIPTION OF THE INVENTION

Embodiments of the present invention will now be described with reference to the accompanying drawings. Radiation in the present invention includes X-rays. The following description will be made on an X-ray CT apparatus as an example of the radiation CT apparatus.

Apparatus Configuration

Figure 1:
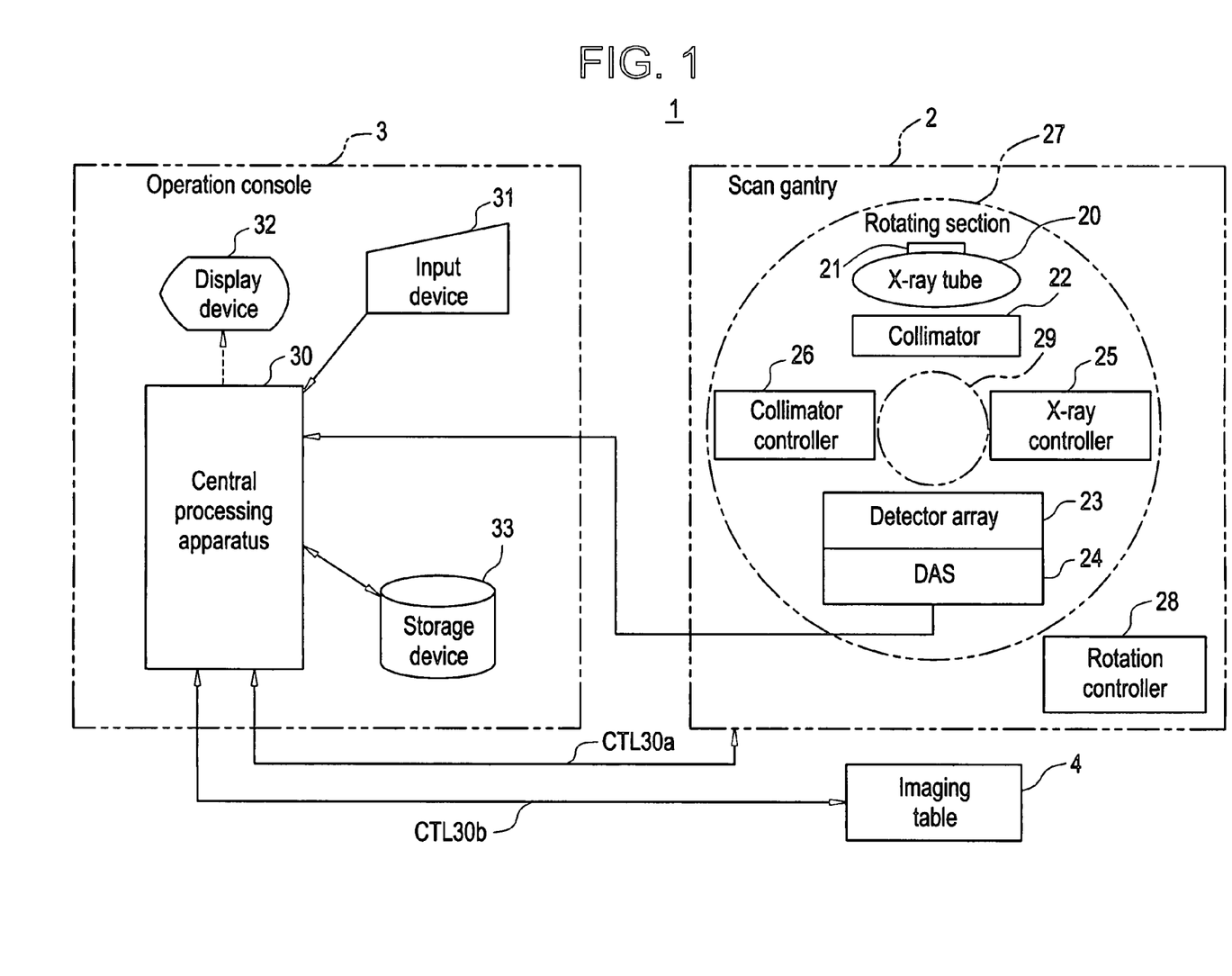
FIG. 1 shows the apparatus configuration of one embodiment of an X-ray CT apparatus in accordance with the present invention.
Figure 2:
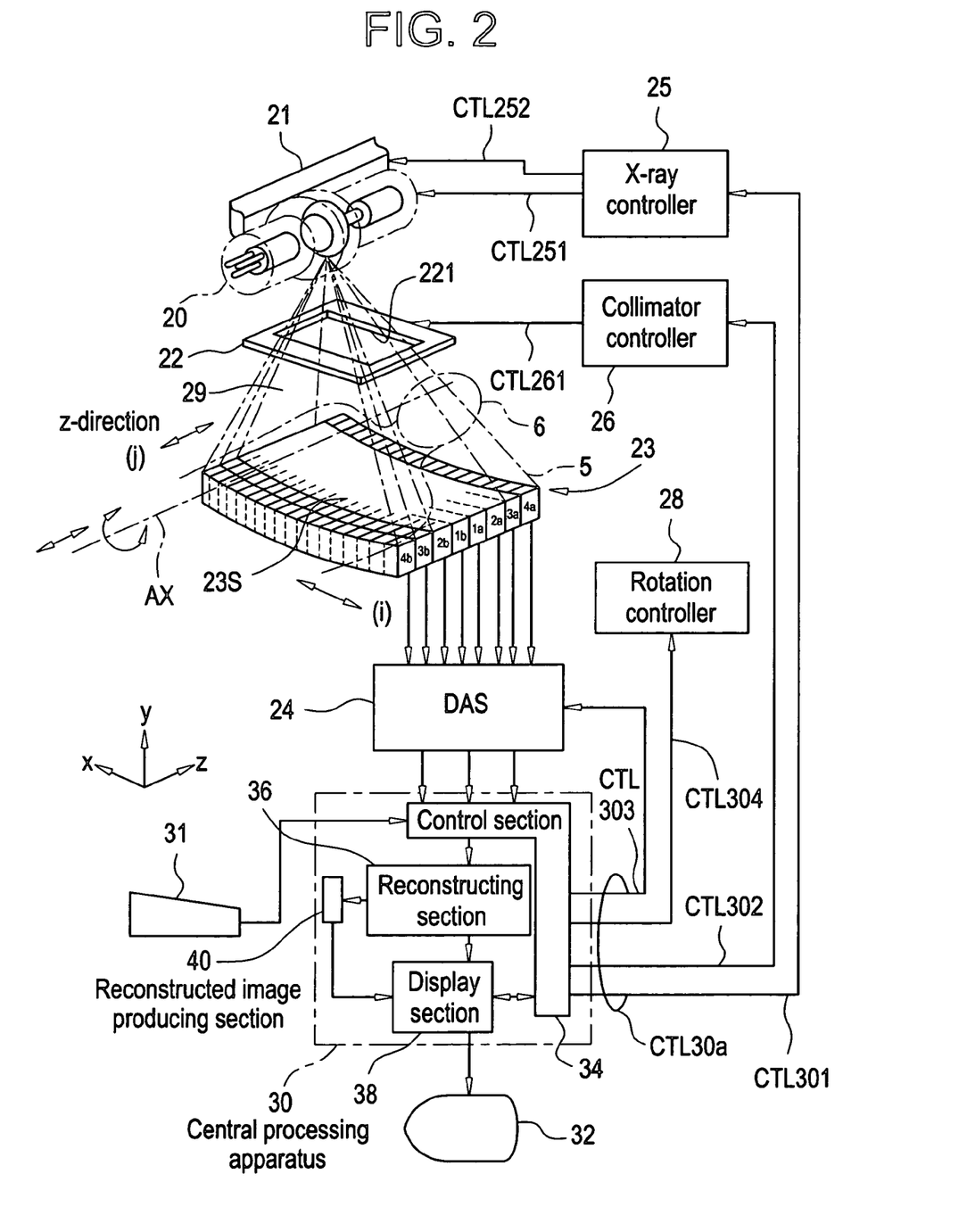
FIG. 2 shows the configuration of a main portion in the X-ray CT apparatus shown in FIG. 1.

FIG. 1 shows the apparatus configuration of an embodiment of an X-ray CT apparatus in accordance with the present invention, and FIG. 2 shows the configuration of a main portion in the X-ray CT apparatus shown in FIG. 1. The X-ray CT apparatus I shown in FIG. 1 is an embodiment of the radiation computed tomography apparatus in the present invention.

As shown in FIG. 1, the X-ray CT apparatus 1 in accordance with the present embodiment comprises a scan gantry 2, an operation console 3, and an imaging table 4.

The scan gantry 2 comprises an X-ray tube 20, a moving section 21, a collimator 22, a detector array 23, a data acquisition system (DAS) 24, an X-ray controller 25, a collimator controller 26, a rotating section 27, and a rotation controller 28.

The X-ray tube 20 is an embodiment of the radiation tube in the present invention, and the moving section 21, rotating section 27 and rotation controller 28 constitute an embodiment of the moving means in the present invention.

Moreover, the X-ray tube 20, moving section 21, detector array 23, rotating section 27 and rotation controller 28 constitute an embodiment of the radiation detecting apparatus in the present invention.

As shown in FIG. 2, the X-ray controller 25 is connected to the X-ray tube 20 and X-ray tube moving section 21. The collimator controller 26 is connected to the collimator 22. The detector array 23 is connected to the DAS 24, and the rotation controller 28 is connected to the rotating section 27.

The X-ray tube 20 emits X-rays toward the collimator 22 at an intensity determined based on a control signal CTL251 from the X-ray controller 25.

The collimator 22 modifies the emission extent of the X-rays emitted by the X-ray tube 20 through adjustment of the degree of openness of an aperture 221 based on a control signal CTL261 from the collimator controller 26.

In the present embodiment, the degree of openness of the aperture 221 is adjusted so that the whole two-dimensional X-ray detection surface of the detector array, which will be discussed below, is irradiated with X-rays.

The detector array 23 comprises a plurality of X-ray detectors to form a two-dimensional matrix (array) having i columns and j rows.

Each X-ray detector is made of a combination of a scintillator and a photodiode, for example.

In the column direction, approximately i=1000 X-ray detectors are arranged to constitute one detector row. FIG. 2 shows the detector array 23 having, by way of example, eight detector rows, i.e., j=8. The detector rows are designated hereinbelow as detector rows 1a, 2a, 3a and 4a sequentially from the center to the right in the row direction of the detector array 23, and as detector rows 1b, 2b, 3b and 4b sequentially from the center to the left.

The plurality of detector rows 1a–4a and 1b–4b are adjoined in parallel with one another.

By thus arranging the X-ray detectors in a matrix, a generally two-dimensional X-ray detection surface 23S is formed.

As shown in FIGS. 1 and 2, the detector array 23 is disposed at a certain distance from the collimator 22. The space between the collimator 22 and detector array 23 forms an X-ray emission space 29. The X-ray emission space 29 receives a subject 6.

The detector array 23 detects on the X-ray detection surface 23S the intensity of an X-ray beam 5 emitted at the aperture 221 of the collimator 22 and passing through the X-ray emission space 29 receiving therein the subject 6.

The DAS 24 collects detected data for the X-ray intensity from the individual X-ray detectors constituting the X-ray detection surface 23S based on a control signal CTL303 from the operation console 3, and sends the data to the operation console 3. The detected data collected by the DAS 24 is sometimes referred to as raw data.

The DAS 24 A–D (analog-to-digital) converts the raw data and sends it to the operation console 3.

The rotating section 27 rotates around a predefined axis of rotation AX of the X-ray emission space 29 based on a control signal from the rotation controller 28.

The rotating section 27 supports the X-ray tube 20, moving section 21, collimator 22, detector array 23, DAS 24, X-ray controller 25 and collimator controller 26, and rotates around the axis of rotation AX by rotation of the rotating section 27 while maintaining the relative positional relationship among these components.

In the present embodiment, the detector rows in the detector array 23 are arranged along the direction of the axis of rotation AX. The direction of the axis of rotation AX, i.e., the direction of the arrangement of the detector rows 1a–4a and 1b–4b in the detector array 23, is defined as a z-direction.

The X-ray tube 20 and detector array 23 are disposed so that the emission center of X-rays in the X-ray tube 20 is aligned with the center of the detector array 23 in the z-direction.

The moving section 21 moves the X-ray tube 20, collimator 22 and detector array 23 in the z-direction based on a control signal CTL252 from the X-ray controller 25 while maintaining their relative positional relationship.

The subject 6 is laid on the imaging table 4. The position of the imaging table 4 can be changed by a motor, for example, and the imaging table 4 carries the subject 6 into the X-ray emission space 29 in response to a control signal CTL30b from the operation console 3. The subject 6 is carried into the space 29 so that the direction of the subject's body axis running from head to toe is aligned with the z-direction, for example.

The X-ray controller 25 outputs the control signal CTL251 for controlling the X-ray intensity emitted by the X-ray tube 20 and the control signal CTL252 for controlling the moving section 21, based on a control signal CTL301 from the central processing apparatus 30 in the operation console 3, which will be discussed later.

The X-ray controller 25 moves the moving section 21 at a predefined pitch in the z-direction in response to the control signal CTL252.

The collimator controller 26 controls the degree of openness of the aperture 221 by the control signal CTL261 output to the collimator 22 in response to a control signal CTL302 from the operation console 3.

In the present embodiment, the degree of openness of the aperture 221 is adjusted so that the X-ray beam 5 passing through the collimator 22 is emitted over the whole X-ray detection surface 23S of the detector array 23.

The rotation controller 28 outputs a control signal to the rotating section 27 based on a control signal CTL304 from the central processing apparatus 30 in the operation console 3 to rotate the rotating section 27 around the axis of rotation AX.

In the present embodiment, for example, one scan is conducted by the detector array 23 detecting the X-ray intensity in all views around the axis of rotation AX during one rotation of the rotating section 27 at a predefined position on the axis of rotation AX.

As shown in FIG. 1, the operation console 3 comprises a central processing apparatus 30, an input device 31, a display device 32, and a storage device 33.

The input device 31 accepts a command input by an operator for operating the X-ray CT apparatus 1, and sends the command to the central processing apparatus 30.

The display device 32 is for displaying a CT image resulting from a calculation by the central processing apparatus 30.

The storage device 33 stores several kinds of programs and parameters for operating the X-ray CT apparatus 1 via the central processing apparatus 30, and data including image data for a CT image.

As shown in FIG. 2, the central processing apparatus 30 comprises a control section 34, a reconstructing section 36, a display section 38, and a reconstructed image producing section 40.

The reconstructing section 36 is one embodiment of the image reconstructing means, and the reconstructed image producing section 40 is one embodiment of the reconstructed image producing means in the present invention.

The central processing apparatus 30 may be constituted as a single hardware unit or as a system comprised of a plurality of appropriate hardware units corresponding to the aforementioned components.

The control section 34 is connected with the DAS 24, input device 31, reconstructing section 36, display section 38, X-ray controller 25, collimator controller 26, rotation controller 28 and imaging table 4.

The reconstructing section 36 is further connected to the display section 38 and reconstructed image producing section 40, and the display section 38 and reconstructed image producing section 40 are connected to each other.

The storage device 33 is appropriately accessed by the components of the central processing apparatus 30.

The control section 34 outputs the control signal CTL30b to the imaging table 4 to carry the subject 6 into the X-ray emission space 29.

The control section 34 outputs a control signal CTL30a to the scan gantry 2 based on a command input by the operator via the input device 31 for acquiring detected data for use in producing a tomographic image of the subject 6 as a CT image, and causes the gantry 2 to conduct a scan on the subject 6. The control signal CTL30a from the control section 34 includes the control signals CTL301, 302, 303 and 304.

The control section 34 receives the detected data collected by the DAS 24 in a scan.

The reconstructing section 36 reconstructs a tomographic image of a region to be examined in the subject 6 based on the detected data obtained via the control section 34.

An example of a scan on the subject 6 by the scan gantry 2 via the control section 34, and production of a tomographic image of the subject 6 by the reconstructing section 36 will be described later in detail.

The reconstructed image producing section 40 performs multiplanar reformation based on the tomographic image data reconstructed by the reconstructing section 36 in response to a command from the control section 34 via the reconstructing section 36, and produces a tomographic image in a direction different from that for the tomographic image reconstructed by the reconstructing section 36.

The display section 38 displays the tomographic image produced by the reconstructing section 36 and/or that produced by the reconstructed image producing section 40 on the display device 32 in response to a command signal from the control section 34.

Tomographic Image Production

Now a scan on a region to be examined in the subject 6 by the scan gantry 2, and tomographic image production based on detected data acquired in the scan will be described in detail.

FIG. 3 is a diagram for explaining a method of producing a tomographic image in the present embodiment, in which (a) shows a relationship between an X-ray beam and a tomographic image in a plane containing the z-axis, and (b) shows a perspective view of a plurality of tomographic images.

Figure 3A:
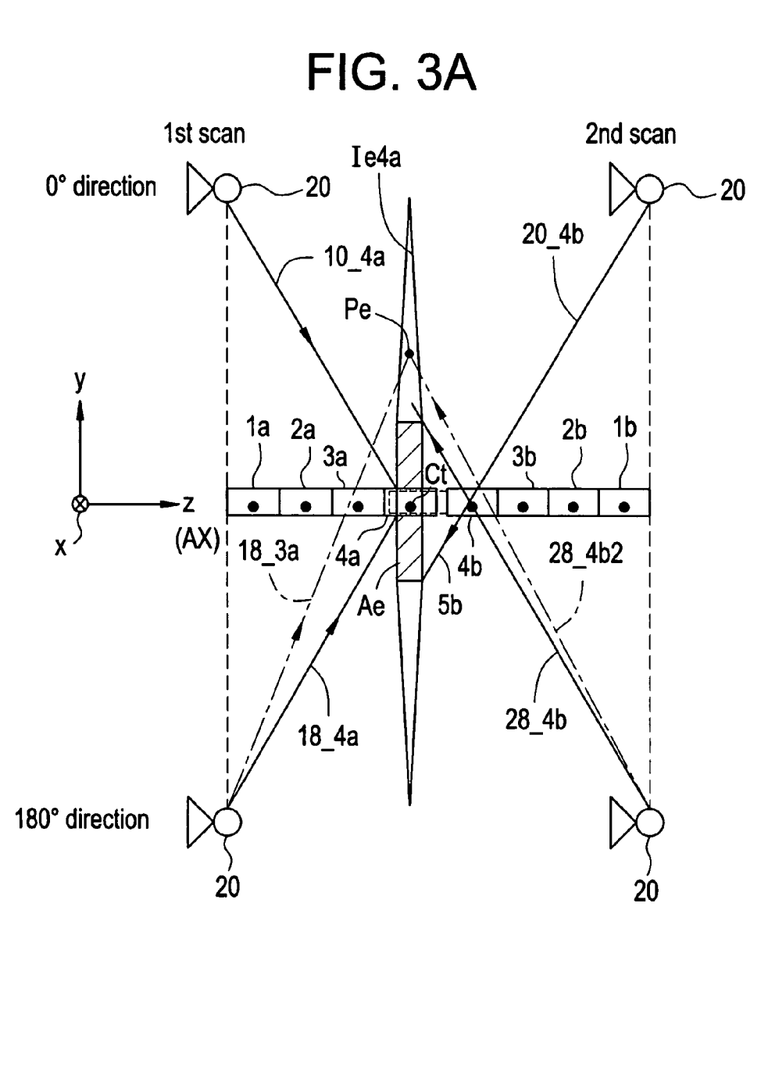
FIG. 3 is a diagram for explaining a method of producing tomographic images in one embodiment of the present invention, in which (a) shows a relationship between an X-ray beam and a tomographic image in a plane containing the z-axis, and (b) is a perspective view of the tomographic images.
Figure 3B:
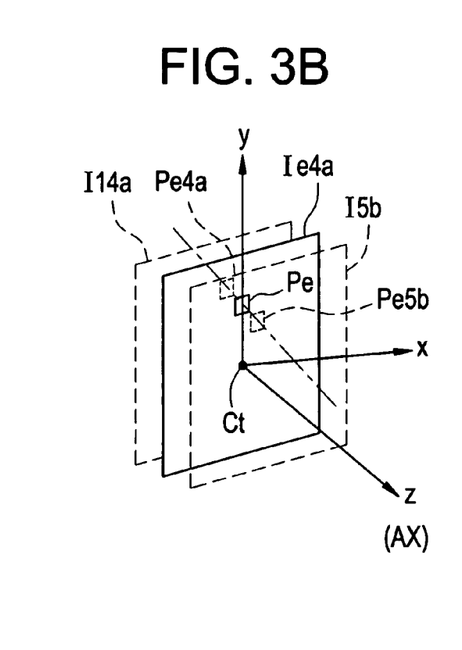
Figure 4:
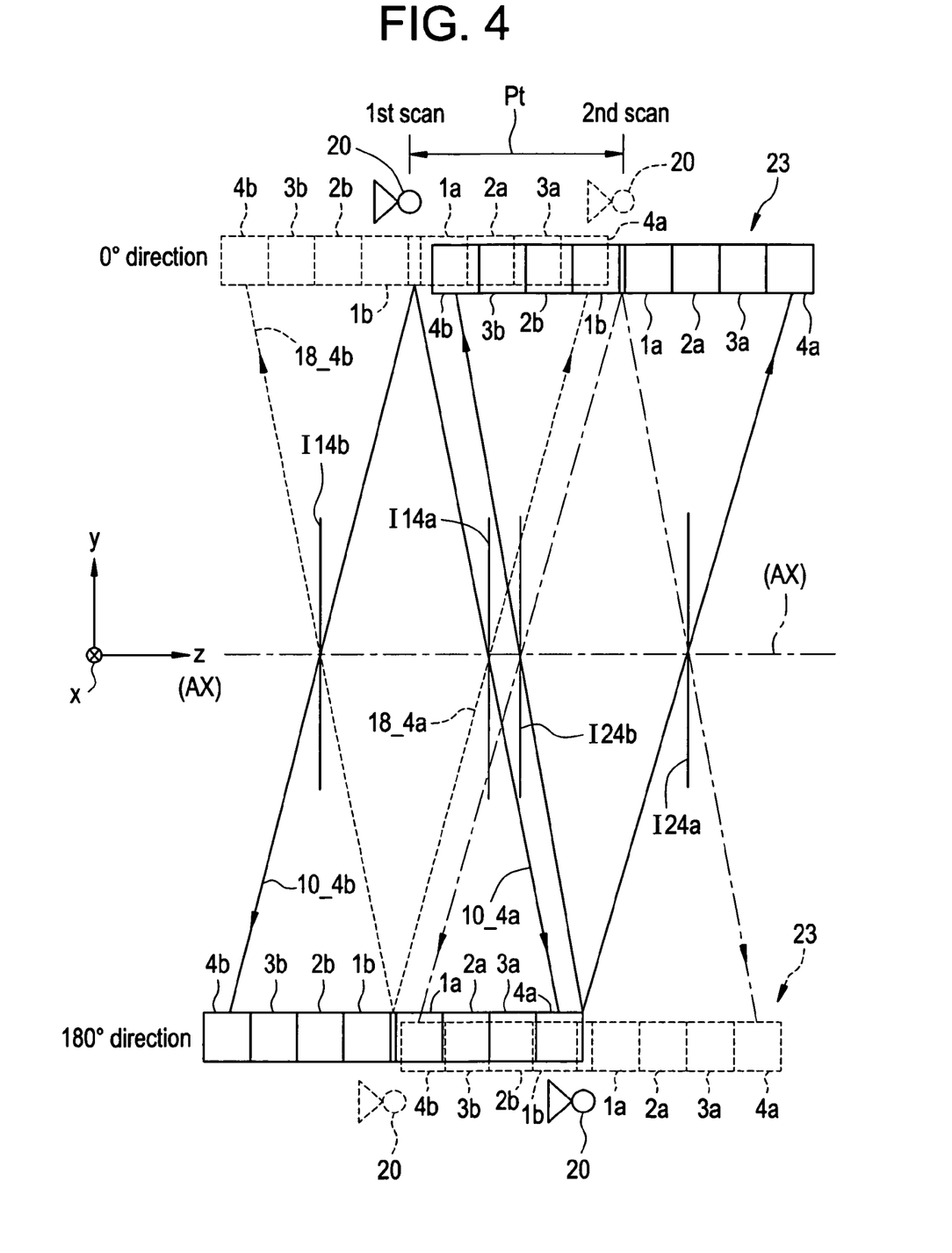
FIG. 4 is a diagram for explaining the idea of FIG. 3(*a*).

FIG. 4 is a diagram for explaining the idea of FIG. 3(*a*). Thus, FIG. 4 will be first explained hereinbelow.

As previously discussed, the X-ray tube 20 and detector array 23 rotate around the axis of rotation AX. In FIG. 4, the axis of rotation AX is defined as the z-axis.

Moreover, in FIG. 4, the initial position of the X-ray tube 20 is defined as the 0° direction, and the position of the X-ray tube 20 after rotation from the initial position by 180° around the z-axis as the 180° direction. Furthermore, the y-direction is defined so that the plane containing the 0° and 180° directions is the yz-plane. The x-direction is defined as the direction orthogonal to the drawing plane of FIG. 4.

In the present embodiment, the control section 34 causes the scan gantry 2 to conduct scanning generally referred to as axial scanning, in which one scan is conducted at a predefined position along the z-axis direction, and a next scan is conducted thereafter at a position shifted at a predefined pitch along the z-axis. In FIG. 4, a case in which two scans are conducted is shown.

The control section 34 outputs the control signal CTL301 to the X-ray controller 25 to emit X-rays from the X-ray tube 20. The control section 34 also outputs the control signal CTL302 to the collimator controller 26 to adjust the degree of openness of the aperture 221 of the collimator 22 so that all the X-ray detector rows 1*a*–4*a* and 1*b*–4*b* are irradiated with an X-ray beam. In the present embodiment, an X-ray beam generally referred to as a fan beam that has a fan-like cross-sectional shape in the yz-plane is projected to the detector array 23, as shown in FIG. 4.

In this condition, the control section 34 outputs the control signal CTL304 to the rotation controller 28 for causing the rotating section 27 to rotate and conducts a scan, and outputs the control signal CTL303 to the DAS 24 for collecting detected data acquired by the detector array 23.

Thus, detected data, i.e., raw data, in all views around the z-axis are collected by the DAS 24. The raw data corresponds to X-ray projection data for a region to be examined.

The reconstructing section 36 applies backprojection processing to the raw data to reconstruct a tomographic image of the region to be examined.

However, if the raw data is used in the backprojection as it is, the reconstructed tomographic image suffers from blurring or noise. Thus, the reconstructing section 36 processes the raw data by applying FFT (fast Fourier transformation) to the raw data to transform the data into those in the frequency domain, applying filtering for reducing the blurring or noise, and then recovering the original format of the raw data through IFFT (inverse fast Fourier transformation).

The reconstructing section 36 applies backprojection to the processed raw data to reconstruct a tomographic image.

The reconstructing section 36 reconstructs tomographic images orthogonal to the axis of rotation AX at respective positions at which an X-ray beam emitted from the X-ray tube 20 and impinging upon the detector rows 1*a*–4*a* and 1*b*–4*b* intersects the axis of rotation AX.

For example, the tomographic image I14b shown in FIG. 4 represents a tomographic image of the region to be examined at a perpendicular position at which an X-ray beam 10_4b from the 0° direction toward a detector row 4b lying in the 180° direction and an X-ray beam 18_4b from the 180° direction toward a detector row 4b lying in the 0° direction intersect the axis of rotation AX in a first scan. Similarly, the tomographic image I14a represents a tomographic image of the region to be examined at a perpendicular position at which X-ray beams 10_4a and 18_4a from the 0° and 180° directions, respectively, impinging upon a detector row 4a intersect the axis of rotation AX in the first scan.

From the preceding description, it can be seen that eight tomographic images are obtained corresponding to the detector rows 1*a*–4*a* and 1*b*–4*b* in one scan in the present embodiment.

After the one scan has been completed, the control section 34 outputs the control signal CTL301 to the X-ray controller 24 to move the X-ray tube 20, collimator 22 and detector array 23 at a pitch Pt in the z-direction. After the movement by the moving section 21 in the z-direction, the control section 34 outputs the control signals CTL304 and CTL303 to the rotation controller 28 and DAS 24, respectively, to conduct a second scan.

The control section 34 thus causes the scan gantry 2 to achieve axial scanning.

Tomographic images I24b and I24a in FIG. 4 represent tomographic images at positions corresponding to the detector rows 4b and 4a, respectively, in the second scan.

The pitch Pt is predetermined so that the distance between tomographic images lying near a border between scans falls within a certain range. Specifically, the distance between the tomographic images I14a and I24b falls within a certain range, for example.

As described above, tomographic images corresponding to the detector rows 1*a*–4*a* and 1*b*–4*b* with the center of the tomographic images lying at the axis of rotation AX are reconstructed and produced. FIG. 3(*a*) is a variant of FIG. 4 for intuitively showing which detector row a tomographic image on the z-axis corresponds to, in which drawing the detector rows 1*a*–4*a* and 1*b*–4*b* are depicted on the axis of rotation AX that coincides with the z-axis. The positional relationship among the X-ray tube 20 and x-, y- and z-axes is the same as in FIG. 4.

In the present embodiment, the pitch Pt is determined so that the detector row 4b in the second scan is continued from the detector row 4a in the first scan, as shown in FIG. 3(a). The purpose of this is that the distance between tomographic images at the first and last ends of the scans is made approximately equal to that between other tomographic images, and the largest possible extent may be imaged in the z-direction in each scan to reduce the imaging time.

In FIG. 3(a), when an X-ray beam emitted from the X-ray tube 20 passes through a certain detector row depicted in FIG. 3(a), this means that the X-ray beam actually enters that detector row lying at a position across the axis of rotation AX. For example, in a first scan shown in FIG. 3(a), an X-ray beam 10_4a shown to be passing through the detector row 4a on the axis of rotation AX from the 0° direction actually enters the detector row 4a lying in the 180° direction.

Therefore, it can be seen that which detector row a tomographic image on the axis of rotation AX corresponds to can be recognized by representing the detector rows 1a–4a and 1b–4b on the axis of rotation AX.

For example, consider a case in which a tomographic image at the detector row 4a shown in FIG. 3(a) is to be produced.

In brief, in the present embodiment, image data for tomographic images I14a and I5b at a position corresponding the detector row 4a, as shown in FIG. 3(b), are first reconstructed based on detected data in the first and second scans. Then, the resulting image data of the tomographic images I14a and I5b are combined to generate image data for a final tomographic image Ie4a at a position corresponding to the detector row 4a.

FIG. 3(b) shows that the tomographic images I14a, Ie4a and I5b lie in respective planes parallel to the xy-plane, and pixels Pe4a, Pe and Pe5b in the tomographic images I14a, Ie4a and I5b correspond to the region to be examined at the same position.

Data generation for the tomographic image Ie4a will now be described in detail.

First, let us consider data reconstruction by the reconstructing section 36 for the tomographic image I14a using detected data in the first scan. As can be clearly seen from FIG. 3(a), in the yz-plane, for example, a region to be examined through which the X-ray beams 10_4a and 18_4a actually detected by the detector row 4a have passed is only a point Ct on the axis of rotation AX.

Therefore, the reconstructing section 36 reconstructs the tomographic image I14a corresponding to the detector row 4a by a cone BP (backprojection) process. In the first scan, for example, an X-ray beam 18_3a passing through the region to be examined at a position corresponding to the pixel Pe in FIGS. 3(a) and (b) is detected by the detector row 3a. The reconstructing section 36 reconstructs image data of a pixel Pe4a representing the same region to be examined as that of the pixel Pe in the tomographic image I14a using detected data acquired by the detector row 3a.

Moreover, image data of pixels from the pixel corresponding to the point Ct through the pixel Pe4a in the tomographic image I14a are reconstructed based on raw data obtained by interpolation between detected data from the detector rows 4a and 3a in the first scan, for example.

By such a cone BP process, the reconstructing section 36 reconstructs image data for the tomographic image I14a.

The reconstructing section 36 also reconstructs the tomographic image corresponding to the detector row 4a using detected data in the second scan, as in the first scan. To this end, it is assumed that an imaginary detector row 5b exists adjacent to the end of the detector array 23 lying at the second scan position on the side nearest to the first scan, as shown in FIG. 3(a). The reconstructing section 36 reconstructs the tomographic image I5b corresponding to the detector row 5b.

This means that the tomographic image corresponding to the detector row 4a in the first scan is reconstructed also using detected data in the second scan, because the position of the detector row 5b is the same as that of the detector row 4a in the first scan.

The outermost X-ray beams in the second scan are X-ray beams 20_4b and 28_4b, and there is no X-ray beam passing through the cross-hatched region Ae at a position corresponding to the detector row 5b, and hence, detected data thereat cannot be obtained. Thus, the reconstructing section 36 extrapolates detected data from the detector row 4b, for example, and reconstructs image data of pixels corresponding to the region Ae in the tomographic image I5b. For the other regions, image data are reconstructed using detected data from the detector rows 1b–4b and interpolated data thereof.

The reconstructing section 36 thus reconstructs data for the tomographic image I5b by the cone BP process using the detected data in the second scan.

After reconstructing and obtaining the image data for the tomographic images I14a and I5b, the reconstructing section 36 additively combines the image data of the tomographic images I14a and I5b on a pixel-by-pixel basis. For example, the image data for the tomographic image I14a and that for the tomographic image I5b are averaged, and the resulting image data is used as combined image data. The reconstructing section 36 finally produces a combined tomographic image Ie4a at a position corresponding to the detector row 4a based on the combined tomographic image data produced by the combining. When a command to display a CT image at a position corresponding to the detector row 4a is input by the operator, the combined tomographic image Ie4a is displayed on the display device 32 by the control section 34 via the display section 38.

As described above, in the present embodiment, data for one tomographic image is produced using detected data obtained in a plurality of scans at different positions along the z-direction. For example, the pixel Pe in the combined tomographic image Ie4a reconstructed in the present embodiment is reconstructed from data of the X-ray beam 18_3a passing through the detector row 3a in the first scan and data of an X-ray beam 28_4b2 passing through the detector row 4b in the second scan. Thus, the image quality of the pixel Pe is higher than that of the pixel Pe4a reconstructed in the conventional cone BP process using only the data of the X-ray beam 18_3a. As can be clearly seen from the preceding description, the image quality of the combined tomographic image obtained in accordance with the present embodiment is higher than that of a tomographic image obtained by the conventional cone BP process.

Moreover, in the present embodiment, image data of a combined tomographic image is generated by adding image data of tomographic images acquired in a plurality of scans, rather than by combining raw data acquired by the detector array 23. Thus, FFT or other such reconstruction processing is not needed in producing the combined tomographic image, and the computation time is reduced. In addition, the combined tomographic image can be easily obtained.

Since the detector array 23 is irradiated with a fan beam, the amount of detected data usable in reconstruction is smaller in the tomographic image corresponding to the outer detector row in each scan. Thus, the effect of improving image quality is higher in a combined tomographic image corresponding to the more peripheral detector row of the detector array 23 in the z-direction because the amount of usable detected data is increased more there than in the conventional technique.

Weight Determination Method

In the preceding description, combined tomographic image data is generated by averaging tomographic image data acquired in a plurality of scans. However, image quality may be further improved by appropriately weighting the data for the plurality of tomographic images for use in the combining depending upon the position of the combined tomographic image in the z-direction or position of pixels in the combined tomographic image, and combining such data for the plurality tomographic images. The following description will be made on a method of determining the weight assigned to the data for the plurality of tomographic images.

Consider reconstruction of tomographic image data at a position corresponding to the detector row 4a in FIG. 3(a), for example. For simplification, a pixel at the point Ct and a pixel Pe in FIG. 3(a) are considered. The pixel Pe in the combined tomographic image Ie4a is created by combining the pixel Pe4a in the tomographic image I14a in the first scan and the pixel Pe5b in the tomographic image I5b in the second scan.

In the first scan, and for the region to be examined corresponding to the point Ct, there exist detected data by two X-ray beams, i.e., the X-ray beam 10_4a from the 0° direction and X-ray beam 18_4a from the 180° direction, and therefore, a pixel corresponding to the point Ct can be reconstructed with high accuracy.

In the first scan, and for the region to be examined corresponding to the pixel Pe4a, there is no X-ray beam passing from the 0° direction and only detected data by the X-ray beam 18_3a from the 180° direction is available; therefore, it is difficult to reconstruct the pixel Pe4a with high accuracy.

In the second scan, and for the region to be examined corresponding to the point Ct, there is no X-ray beam passing from the 0° or 180° direction, and the pixel corresponding to the point Ct cannot be reconstructed using actual detected data by X-rays passing through the point Ct.

In the second scan, and for the region to be examined corresponding to the pixel Pe5b, there is no X-ray beam passing from the 0° direction, and only detected data by the X-ray beam 28_4b2 from the 180° direction is available; therefore, it is difficult to reconstruct the pixel Pe5b with high accuracy.

Thus, it can be seen that the weight assigned to data for a tomographic image acquired in each scan is preferably changed depending upon the distance from the z-axis so as to improve the image quality of the combined tomographic image.

Especially, in a tomographic image corresponding to the imaginary detector row, there exists a region having no available detected data of X-rays actually passing through the region to be examined, and the weight for the region must be zero. For example, the weight on the tomographic image I5b for the cross-hatched region Ae in FIG. 3(a) is set to zero.

In the following description, the dimensions of the region for which the weight is set to zero in the tomographic image corresponding to the imaginary detector row will be actually derived with reference to FIG. 5.

Figure 5:
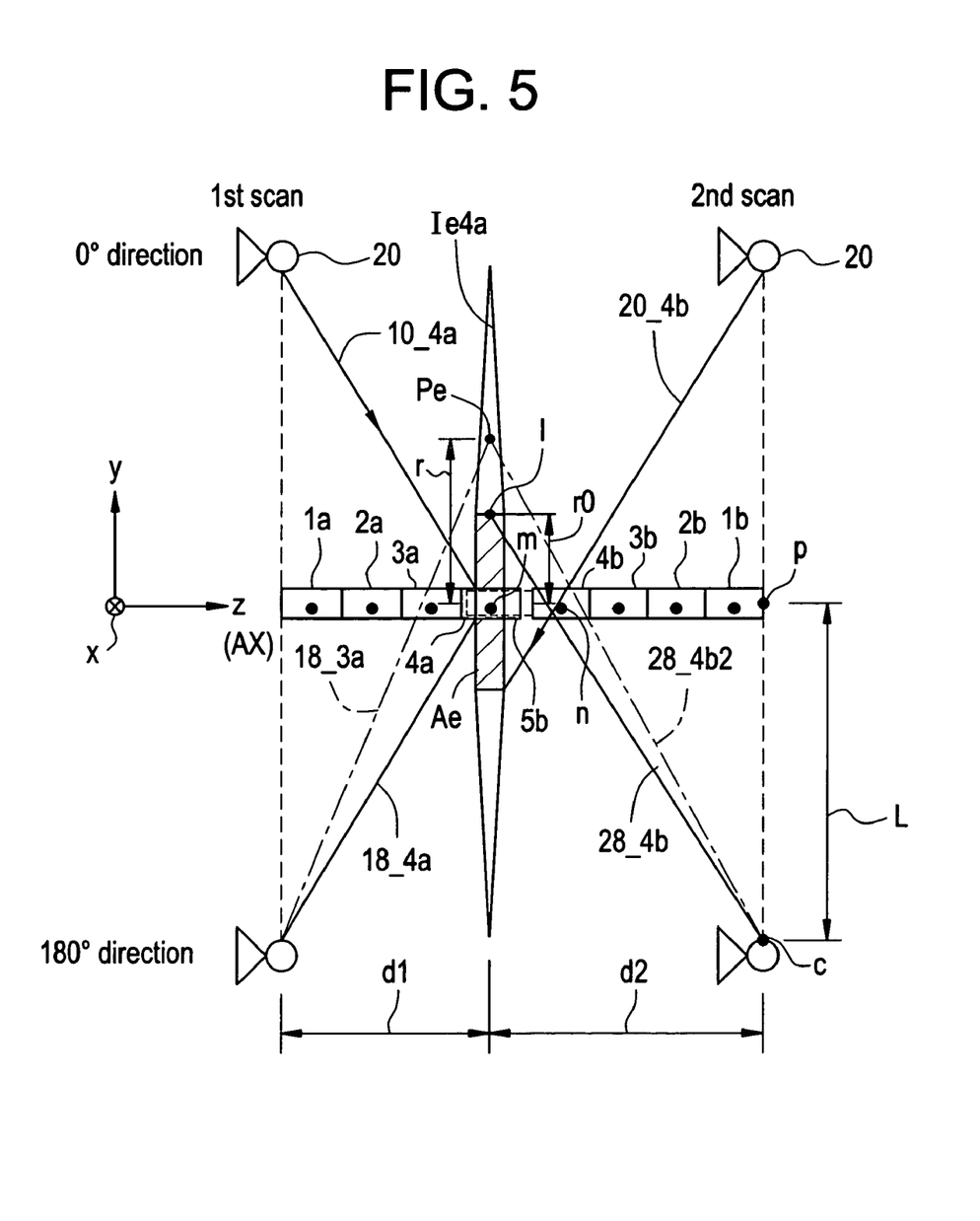
FIG. 5 is a diagram for deriving a region having a weight of zero in a tomographic image.

FIG. 5 is a diagram for deriving the region for which the weight is set to zero, and it is basically the same as FIG. 3(a). Thus, similar portions are designated by similar symbols, and detailed description therefor will be omitted.

As shown in FIG. 5, the distance on the z-axis from the emission center of the X-ray tube 20 in the first scan projected onto the z-axis to a combined tomographic image to be produced is defined as d1. Moreover, the distance on the z-axis from the emission center of X-ray tube 20 in the second scan projected onto the z-axis to the combined tomographic image to be produced is defined as d2.

Furthermore, the distance from the emission center of the X-ray tube 20 to the z-axis is defined as L.

The distances d1, d2 and L can be geometrically determined from the apparatus configuration of the scan gantry 2. These distance values are stored in the storage device 33, for example.

Now consider the triangle lmn and the triangle nop in FIG. 5. The length of the side np in the triangle nop is d1. Therefore, the length of the side mn in the triangle lmn is (d2−d1). Since the triangle lmn is similar to the triangle nop, the length of the side lm in the triangle lmn can be found from the ratio between the sides, i.e., the length is [L(d2−d1)/d1]. The reconstructing section 36 accesses data of the distances d1 and d2 and distance L in the storage device 33 corresponding to the position in the z-direction of the combined tomographic image to be produced, and calculates the length of the side lm. The length of the side lm is the distance r0 from the z-axis at which the weight is set to zero in a tomographic image corresponding to the imaginary detector row.

For the region having a weight of zero in the tomographic image corresponding to the imaginary detector row, the weight assigned to tomographic image data corresponding to the other detector rows for use in producing the combined tomographic image data is set to one.

For a region having a distance r greater than the distance r0 from the z-axis in the combined tomographic image, the weights assigned to data for the tomographic images reconstructed in the scans are appropriately changed with the distance r.

Moreover, since the distance r0 is a function of the distances d1 and d2, the weights assigned to data for the tomographic images reconstructed in the scans are preferably changed also with the position of the tomographic image to be reconstructed in the z-direction for improving image quality.

As described above, in the present embodiment, the weight assigned to image data of each tomographic image is changed with the position in the z-direction of the tomographic image reconstructed in each of the plurality of scans and with the distance in the tomographic image from the z-axis.

FIG. 6 is a graph showing exemplary variation of the weight, in which (a) shows variation of the weight depending upon the distance from the point Ct on the z-axis for a tomographic image corresponding to each detector row, and (b) shows variation of the weight depending upon the distance in the z-axis direction.

Figure 6A:
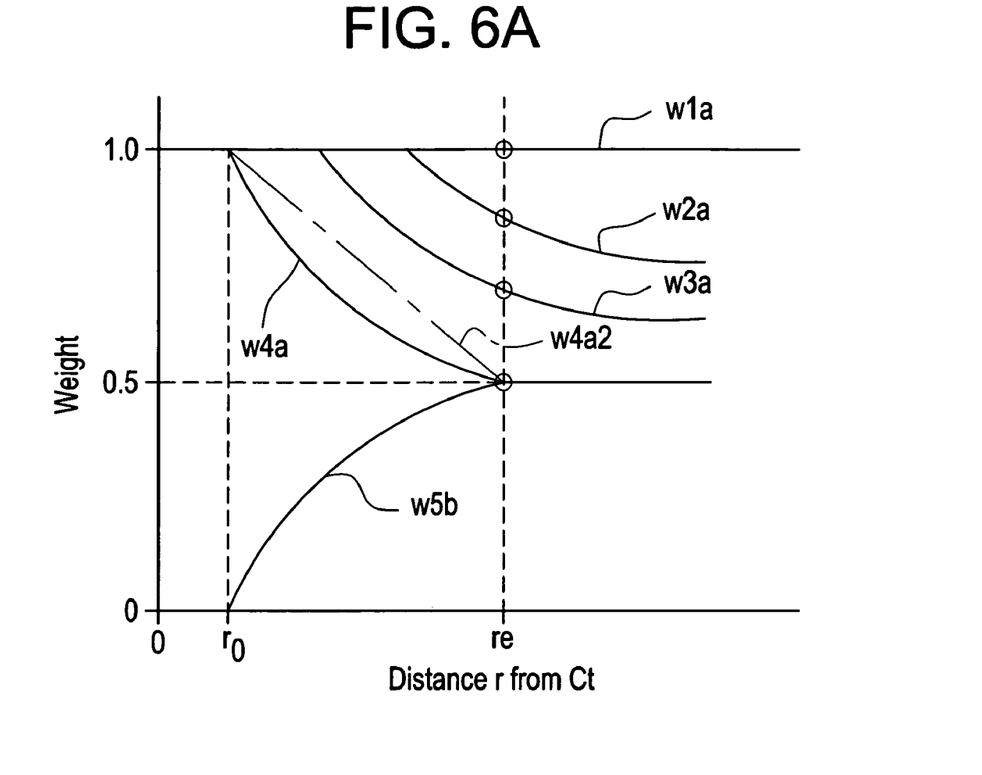
FIG. 6 shows graphs of exemplary variation of the weight, in which (a) shows the weight varying depending upon the distance on the z-axis of tomographic images corresponding to detector rows, and (b) shows the weight varying depending upon the distance in the z-axis direction.

In FIG. 6(a), the horizontal axis represents the distance r from the point Ct on the z-axis, and the vertical axis represents the amount of weight.

Moreover, there are shown exemplary weights w1a–w4a assigned to the tomographic images corresponding to the detector rows 1a–4a and a weight assigned to the tomographic image I5b corresponding to the detector row 5b.

As previously discussed, the weight w5b is zero up to the distance r0. The weight w5b is increased to, for example, 0.5 as the distance r increases from the distance r0.

The weight w4a is one up to the distance r0, and is decreased to, for example, 0.5 as the distance r increases from the distance r0.

The weight assigned to data for each tomographic image at the same position in the z-direction is thus set so that the sum is one.

Moreover, in a tomographic image corresponding to the detector row 1a, for example, near the center portion of the detector array 23 in the z-direction, all pixels can be reconstructed using actual data detected by an X-ray beam passing through the subject corresponding to the pixels. Thus, the weight w1a assigned to data for the tomographic image corresponding to the detector row 1a is set to one throughout, as shown in FIG. 6(a).

As for the weights w2a and w3a, the weight w2a assigned to the inner detector row 2a in the detector array 23 is set to one over a larger range than the weight w3a assigned to the outer detector row 3a. Moreover, the weight w2a is larger than the weight w3a and both are decreased from one as the distance r increases.

Figure 6B:
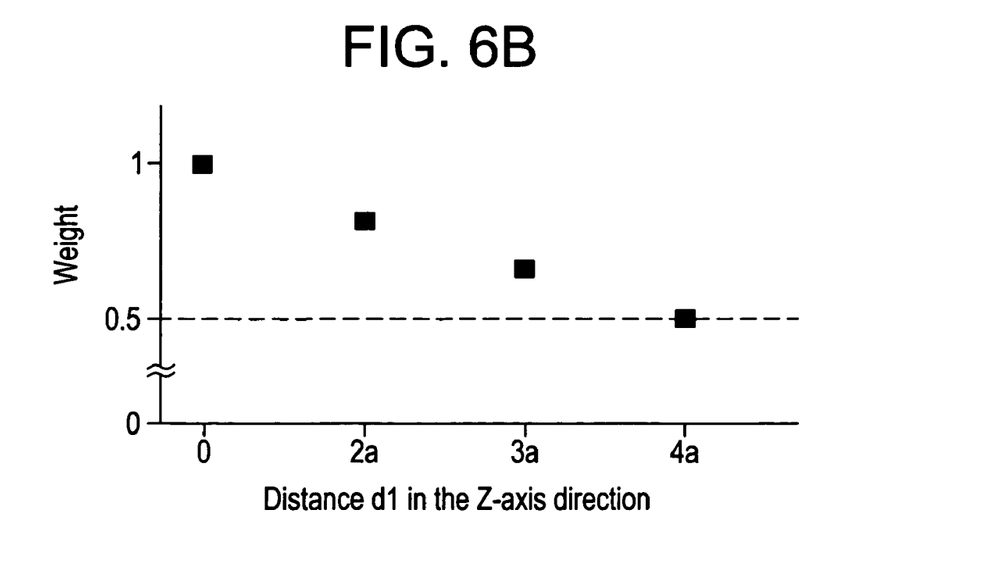

FIG. 6(b) shows a graph in which the weights w1a–w4a are plotted with a constant distance r=re in FIG. 6(a). In FIG. 6(b), the horizontal axis represents the distance d1 from the emission center of the X-ray tube 20 in the z-axis translated into the position of the detector rows 1a–4a, and the vertical axis represents the amount of weight.

As shown in FIG. 6(b), the weight tends to decrease for the outer detector row in the detector array 23. This is because the number of pixels that can be reconstructed using directly detected X-ray intensity data is smaller for a tomographic image corresponding to the outer detector row.

Figure 7A:
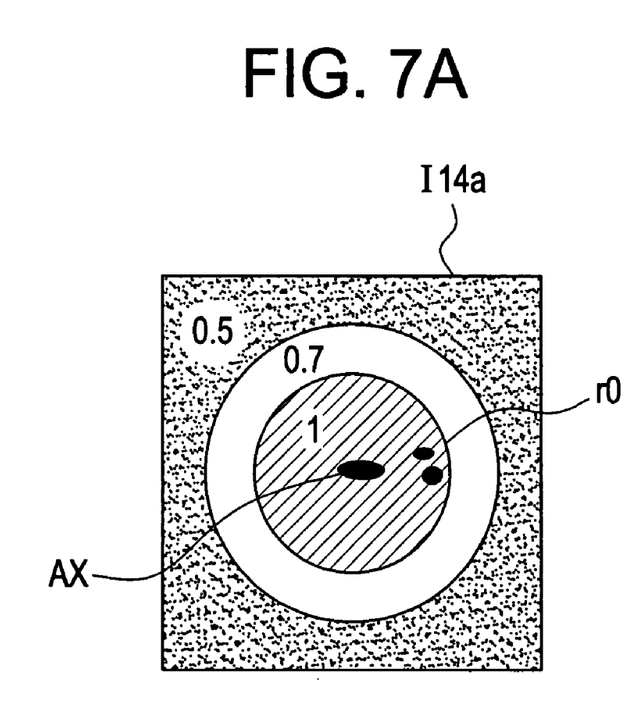
FIG. 7 shows variation of the weight in a tomographic image, in which (a) and (b) show distributions of the weight in different tomographic images.
Figure 7B:
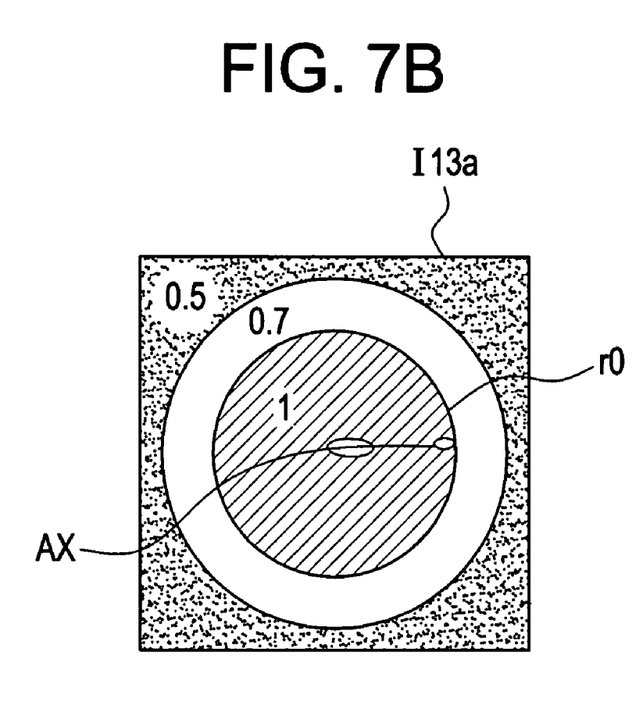

The weight for individual pixels in a tomographic image is changed concentrically from the axis of rotation AX at the center, for example, as shown in FIG. 7. This is because the X-ray emission concentrically varies in the xy-plane centered on the axis of rotation AX due to the X-ray tube 20 rotating around the axis of rotation AX by 360°.

In FIG. 7, (a) shows variation of the weight in the tomographic image I14a corresponding to the detector row 4a, and (b) shows variation of the weight in the tomographic image I13a corresponding to the detector row 3a.

In FIGS. 7(a) and (b), the distributions of the weights w4a and w3a assigned to pixels in the tomographic images I14a and I13a concentrically vary between, for example, 1 and 0.5 centered in the axis of rotation AX as described above.

Moreover, the size of the concentric circles indicating the distribution of each weight varies with the distance in the z-direction. As previously discussed, a tomographic image corresponding to the inner detector row in the detector array 23 has a larger region that can be reconstructed using actual detected data. Thus, the area of the greater weight is larger in the tomographic image I13a than in the tomographic image I14a. For example, the radius r0 that defines an area having a weight of one is larger in the tomographic image I13a than in the tomographic image I14a.

A map of data of the weight concentrically defined corresponding to the detector row as described above is stored in the storage device 33, for example. When calculating combined tomographic image data, the reconstructing section 36 accesses the map, in the storage device 33, of the weight at a position of the combined tomographic image to be produced for each tomographic image for use in the combining. The reconstructing section 36 adds weighted tomographic image data based on the accessed weight map to produce the combined tomographic image data.

While the weight is exemplified as non-linearly changing from one or zero in FIG. 6(a), the weight may be linearly changed, for example, as shown in a plot w4a2 in FIG. 6(a).

Moreover, the weight may be discretely changed; for example, the weight may be one up to a distance r of r0, and 0.5 for a distance larger than r0.

Furthermore, the method of determining the weight is not limited to that described above, and the weight may arbitrarily determined so that the sum of weights on a plurality of pixels for use in the combining is one; for example, w5b+w4a=1.

As described above, the weight is appropriately assigned to tomographic image data for use in the combining depending upon the distance in the z-direction and the distance from the z-axis in the present embodiment. This means that the weight assigned to a pixel is changed with accuracy of reconstruction of that pixel in each tomographic image. Thus, for example, image data for a pixel having high reconstruction accuracy can be fully used to produce combined tomographic image data; consequently, a combined tomographic image is obtained with high image quality.

Moreover, when the weight is concentrically changed as shown in FIG. 7, a map of the weight can be easily generated for each detector row.

Multiplanar Reformation

As described above, the reconstructing section 36 produces a combined tomographic image parallel to the xy-plane at a position corresponding to a certain detector row in the z-direction.

By producing a plurality of such combined tomographic images along the z-direction, a tomographic image in a cross section different from the xy-plane can be produced. The following description will address such multiplanar reformation in detail.

Figure 8A:
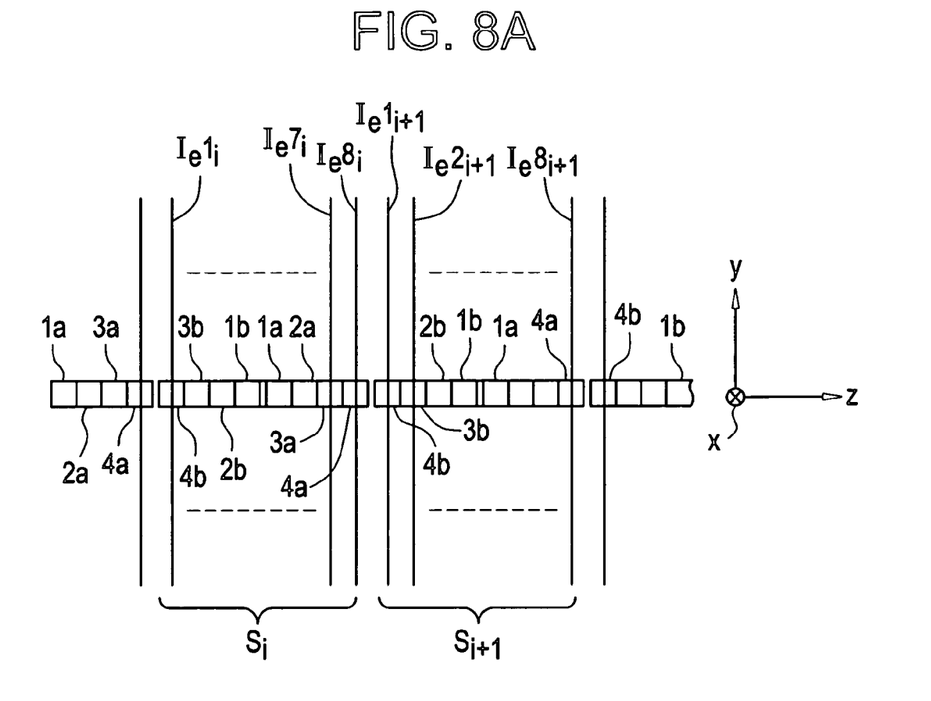
Figure 8B:
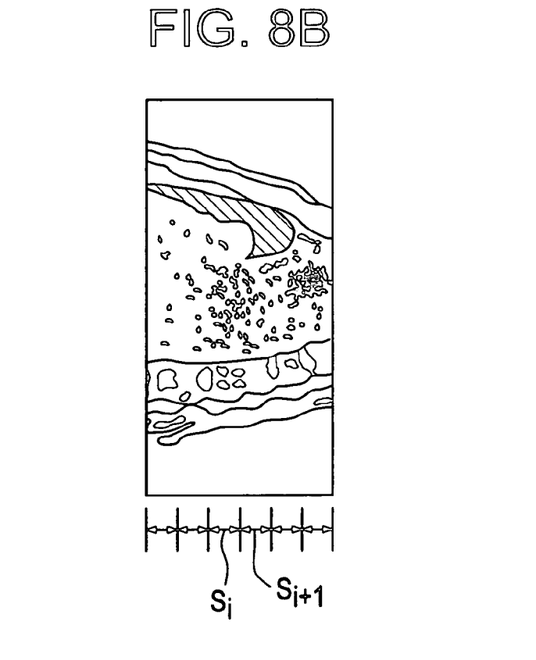

FIG. 8(a) shows production of a plurality of combined tomographic images in the yz-plane in the z-direction, and FIG. 8(b) shows an example of an MPR image in the yz-plane produced using the plurality of combined tomographic images.

In FIG. 8(a), detector rows are depicted over the z-axis, as in FIG. 3(a) and FIG. 5, to indicate the position of combined tomographic images produced in each scan.

As shown in FIG. 8(a), the reconstructing section 36 produces combined tomographic images Ie1i–Ie8i corresponding to the detector rows 4b, 3b, 2b, 1b, 1a, 2a, 3a and 4a in an i-th scan. The eight combined tomographic image are together referred to as a scan image Si.

The reconstructing section 36 also produces combined tomographic images Ie1i+1–Ie8i+1 corresponding to the detector rows 4b, 3b, 2b, 1b, 1a, 2a, 3a and 4a in an (i+1)-th scan. The eight combined tomographic image are together referred to as a scan image Si+1.

The reconstructing section 36 thus produces eight combined tomographic images per scan.

When a command to execute multiplanar reformation is input to the control section 34 by the operator, the reconstructed image producing section 40 accesses image data of combined tomographic images produced by the reconstructing section 36 in each scan. The reconstructed image producing section 40 then gathers all pixels in the yz-plane containing the z-axis among those in the accessed combined tomographic images, and displays them on the display device 32 via the display section 38. An MPR image in the yz-plane is thus obtained, as shown in FIG. 8(b).

Figure 10:
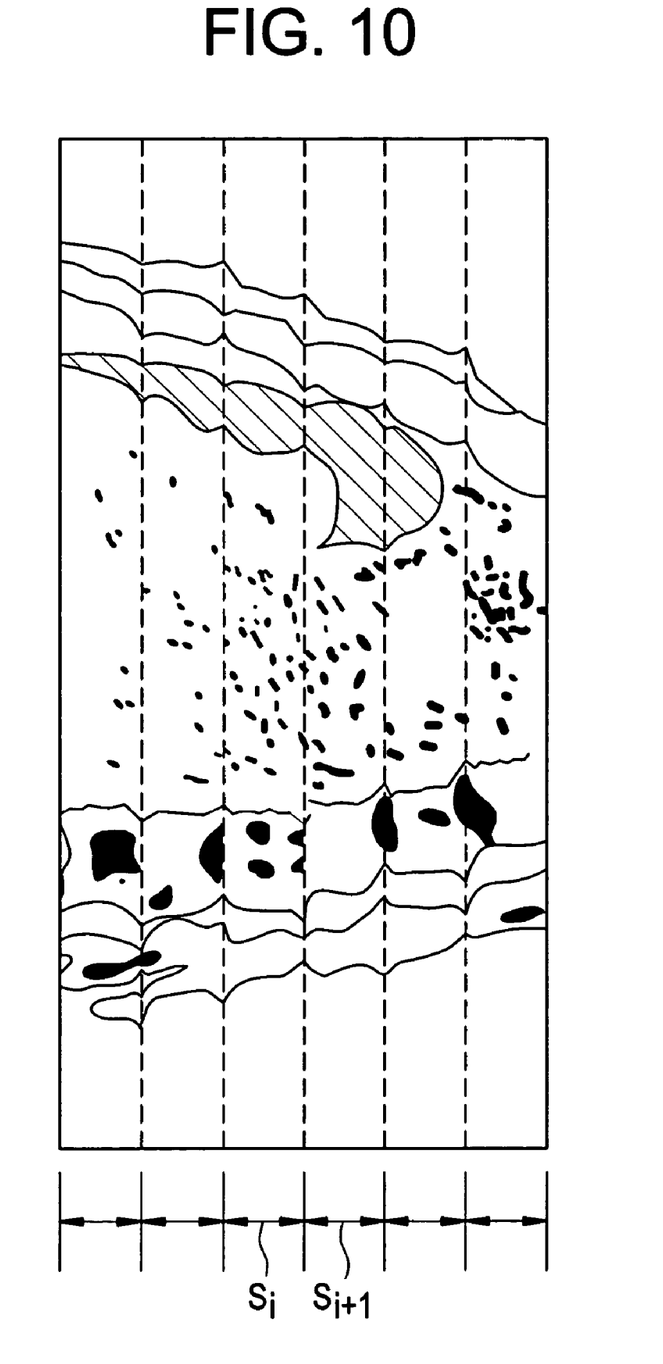
FIG. 10 shows an example of a conventional MPR image.

For comparison, an MPR image obtained by multiplanar reformation using tomographic images reconstructed by the conventional cone BP process is shown in FIG. 10.

As can be seen by comparing FIG. 8(b) with FIG. 10, the MPR image obtained in the present embodiment has a smoother change from pixel to pixel, and banding artifacts, which result from an image offset at the border between scan images as encountered in the conventional MPR image, are suppressed. Moreover, the image quality of each scan image is improved.

As described above, an MPR image is produced using image data of combined tomographic images produced using detected data in each of a plurality of scans at different positions in the z-direction in the present embodiment. Thus, continuity is improved between combined tomographic image data especially at the border between the scans. As a result, an MPR image smoother and having higher image quality than a conventional MPR image is obtained.

Moreover, since the combined tomographic images in the present embodiment have higher image quality than those obtained in the conventional cone BP process, the image quality of scan images constituting the MPR image is improved.

A method of producing a tomographic image in the present embodiment will now be briefly described with reference to a flow chart in FIG. 9.

First, a scan is conducted for obtaining projection data for a region to be examined at a predefined position in the z-axis direction (Step ST1).

Specifically, by rotating the detector array 23 having a plurality of X-ray detectors arranged in a two-dimensional manner around the axis of rotation AX, volumetric data for the subject are acquired.

After one scan has been completed, tomographic image data is reconstructed based on the acquired X-ray detected data (Step ST2).

Specifically, from the detected data acquired for each detector row, image data are reconstructed for a plurality of tomographic images lining up in the z-direction in one scan.

Moreover, tomographic image data corresponding to an imaginary detector row is reconstructed using the detected data acquired in the scan at Step ST1, for use in production of combined tomographic image data.

Weights of appropriately determined magnitude are respectively assigned to image data constituting the plurality of tomographic images acquired at Step ST2 (Step ST3). For example, a weight predefined depending upon the distance in the z-axis direction and the distance from the z-axis is assigned to image data.

Each time a scan has been completed, decision is made as to whether a number of scans sufficient to obtain images in a desired range have been acquired (Step ST4).

If the number of scans is determined to be insufficient, the scan position is shifted in the z-direction at a predefined pitch (Step ST5).

Then, Step ST1 for a scan through Step ST3 for assigning a weight to tomographic image data are executed.

Step ST1–Step ST5 are repeated until a number of scans sufficient to obtain images in a desired range is determined at Step ST4 to be completed.

After all scans have been completed and all image data for tomographic images lining up in the z-direction have been acquired, for example, tomographic images and an imaginary tomographic image lying at the same position in the z-direction are combined (Step ST6).

Specifically, image data for the tomographic images lying at the same position in the z-direction are assigned weights defined for the image data and the weighted data are added to calculate image data for a combined tomographic image.

After obtaining image data of all combined tomographic images in the z-direction, multiplanar reformation is executed to produce an MPR image as needed (Step ST7).

Specifically, an MPR image is obtained by aligning coordinates of the combined tomographic images, and displaying pixels in a predefined plane in a set of those combined tomographic images together.

The tomographic image production procedure is then terminated.

It should be noted that the present invention is not limited to the aforementioned embodiments.

For example, radiation for use in scanning is not limited to X-rays but may be other radiation such as gamma rays.

Moreover, although the number of detector rows is j=8 in the embodiments, the number of rows of the X-ray detectors is not limited thereto but may be j=16 or j=32, for example.

Furthermore, although the moving section 21 is moved in the z-direction to conduct axial scanning in the embodiments, the movement is not limited thereto, and it suffices for the rotating section 27 and subject 6 to be movable relative to each other in the z-direction.

Figure 9:
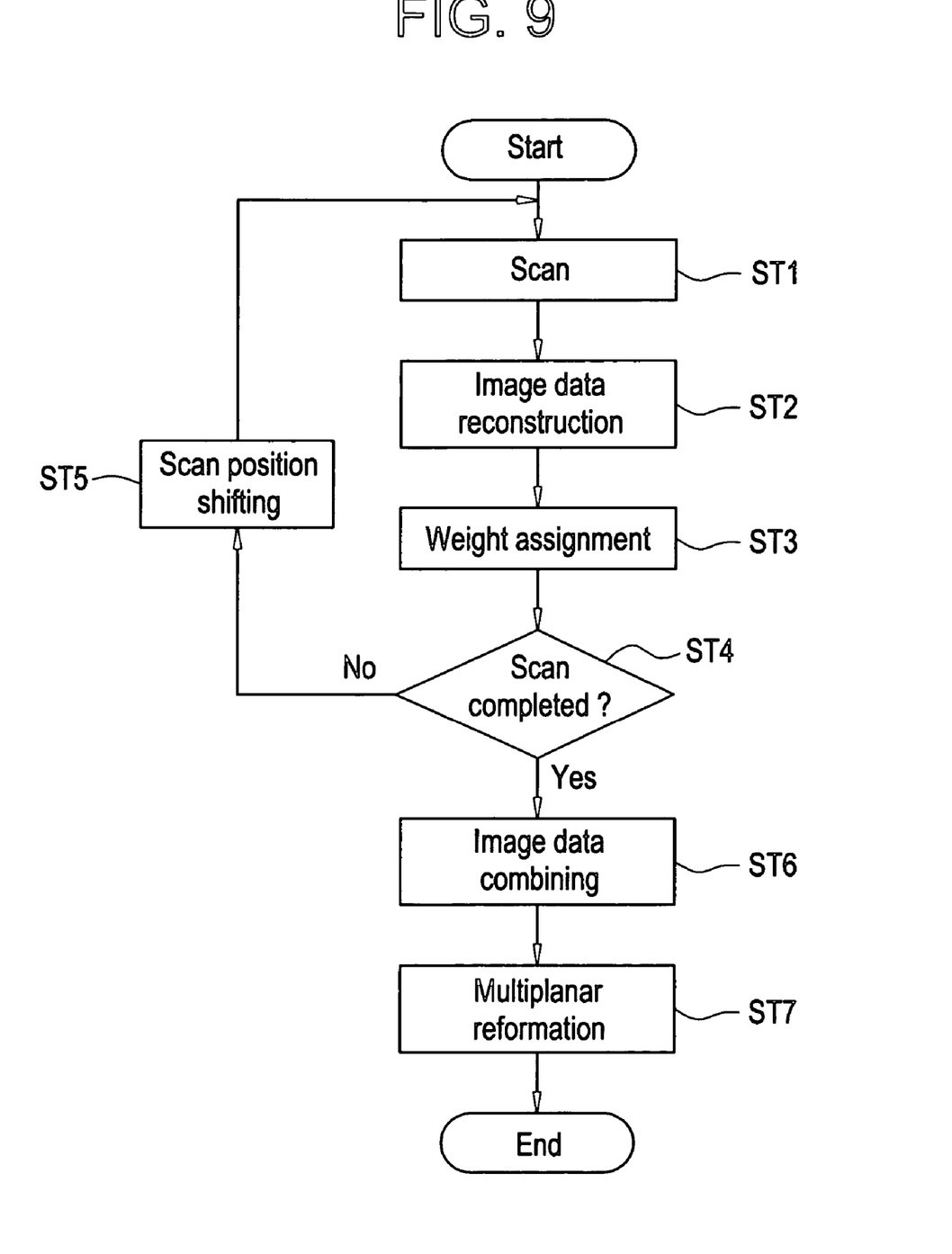
FIG. 9 is a flow chart showing one embodiment of a tomographic image producing method in accordance with the present invention.

Moreover, the flow chart shown in FIG. 9 is merely an example of a tomographic image producing method in accordance with the present invention, and the steps in the flow chart in FIG. 9 may be appropriately shifted within the scope of the appended claims. For example, tomographic images may be reconstructed at a time after all scans have been completed. It is also possible to execute combining of the tomographic images immediately after reconstructing a plurality of tomographic images for use in the combining, rather than after all scans.

Furthermore, the distance need not be one with reference to the z-axis, and a weight for pixels may be changed with the shape of a region to be examined recognized in each tomographic image.

In addition, an MPR image may be produced not only in parallel with the yz-plane but also in parallel with the xz-plane.

Many widely different embodiments of the invention may be configured without departing from the spirit and the scope of the present invention. It should be understood that the present invention is not limited to the specific embodiments described in the specification, except as defined in the appended claims.

The invention claimed is:

1. A radiation computed tomography apparatus comprising:
   a radiation detecting section for conducting a plurality of axial scans for detecting radiation passing through a region to be examined around a predefined axis of said region to be examined at different positions along said predefined axis direction; and
   an image reconstructing device for obtaining a plurality of sets of data for the same position in said region to be examined based on detected data acquired in said plurality of axial scans, and reconstructing data for a first tomographic image of the region to be examined at an image production position in said predefined axis direction based on said plurality of sets of data, wherein said image reconstructing device configured to combine data generated from a first axial scan of said plurality of the axial scans with data generated from a second axial scan of said plurality of the axial scans to reconstruct said first tomographic image, said image reconstructing device generating data for a combined tomographic image by assigning respective weights to said combined data and combining said weighted data for a plurality of tomographic images, and for data for said first tomographic image acquired in said plurality of axial scans at said image production position, a weight is set to zero for data for a pixel among data for pixels in a second tomographic image that lies in a region other than that in which said detected data are present in each said scan.

2. The radiation computed tomography apparatus of claim 1, wherein:
said radiation detecting section comprises:
a radiation tube for emitting the radiation;
a plurality of radiation detectors arranged in a two-dimensional manner around said predefined axis and in a direction along said axis; and
a moving device for rotating said radiation tube and said plurality of radiation detectors around said predefined axis and moving them relative to said region to be examined in the direction along said axis.

3. The radiation computed tomography apparatus of claim 1, wherein:
said respective weights assigned to said data for the plurality of tomographic images are changed depending upon the distance from said predefined axis to each pixel in the tomographic image at said image production position and/or the distance from a predefined position to said image production position on said predefined axis.

4. A radiation computed tomography apparatus comprising:
a radiation detecting section for conducting a plurality of scans for detecting radiation passing through a region to be examined around a predefined axis of said region to be examined at different positions along said predefined axis direction; and
an image reconstructing device for reconstructing, for each of said plurality of scans, data for a tomographic image of the region to be examined at an image production position in said predefined axis direction by a calculation based on detected data acquired in said scan, combining said reconstructed data for a plurality of tomographic images to generate data for a combined tomographic image at said image production position, said image reconstructing device generating said data for the combined tomographic image by assigning respective weights to said data for the plurality of tomographic images at said image production position and combining said weighted data for the plurality of tomographic images, said respective weights assigned to said data for the plurality of tomographic images changed depending upon the distance from said predefined axis to each pixel in the tomographic image at said image production position and/or the distance from a predefined position to said image production position on said predefined axis.

5. The radiation computed tomography apparatus of claim 4, wherein:
said radiation detecting section comprises:
a radiation tube for emitting the radiation;
a plurality of radiation detectors arranged in a two-dimensional manner around said predefined axis and in a direction along said axis; and
a moving device for rotating said radiation tube and said plurality of radiation detectors around said predefined axis and moving them relative to said region to be examined in the direction along said axis.

6. The radiation computed tomography apparatus of claim 4, wherein:
for data for each of said plurality of tomographic images acquired in said plurality of scans at said image production position, the weight is set to zero for data for a pixel among data for pixels in said tomographic image that lies in a region other than that in which said detected data are present in each said scan.

7. The radiation computed tomography apparatus of claim 6, wherein:
the weight assigned to data for the individual pixels in said tomographic image is changed concentrically from said predefined axis at the center.

8. The radiation computed tomography apparatus of claim 4, further comprising:
a reconstructed image producing device for producing a tomographic image in a desired direction based on said data for a plurality of said combined tomographic images generated by said image reconstructing device along said predefined axis direction.

9. A tomographic image producing method comprising the steps of:
conducting a plurality of scans for detecting radiation passing through a region to be examined around a predefined axis of said region to be examined at different positions along said predefined axis direction;
for each of said plurality of scans, calculating and reconstructing data for a tomographic image of the region to be examined at an image production position in said predefined axis direction based on detected data acquired in said scan;
combining said reconstructed data for a plurality of tomographic images to generate data for a combined tomographic image at said image production position, said data for the combined tomographic image generated by assigning respective weights to said data for the plurality of tomographic images and combining said weighted data for the plurality of tomographic images; and
for data for each of said plurality of tomographic images acquired in said plurality of scans at said image production position, setting to zero the weight assigned to data for a pixel among data for pixels in said tomographic image that lies in a region other than that in which said detected data are present in each said scan to facilitate producing a tomographic image.

10. The tomographic image producing method of claim 9, comprising:
changing said respective weights assigned to said data for the plurality of tomographic images depending upon the distance from said predefined axis to each pixel in the tomographic image at said image production position and/or the distance from a predefined position to said image production position on said predefined axis.

11. The tomographic image producing method as defined by claim 9, comprising:
concentrically changing the weight assigned to said data for individual pixels in said tomographic image from said predefined axis at the center.

12. The tomographic image producing method of claim 9, further comprising the steps of:
generating data for a plurality of said combined tomographic images along said predefined axis direction; and
producing a tomographic image in a desired direction based on said data for a plurality of said combined tomographic images.

* * * * *